(12) United States Patent
Mjalli et al.

(10) Patent No.: US 7,022,730 B2
(45) Date of Patent: Apr. 4, 2006

(54) BIS-HETEROARYL ALKANES AS THERAPEUTIC AGENTS

(75) Inventors: Adnan M. M. Mjalli, Jamestown, NC (US); Kathy G. J. Shahbaz, Escondido, CA (US)

(73) Assignee: TransTech Pharma, Inc., High Point, NC (US)

( * ) Notice: Subject to any disclaimer, the term of this patent is extended or adjusted under 35 U.S.C. 154(b) by 0 days.

(21) Appl. No.: 10/273,795

(22) Filed: Oct. 18, 2002

(65) Prior Publication Data

US 2003/0130335 A1  Jul. 10, 2003

Related U.S. Application Data

(60) Provisional application No. 60/348,187, filed on Oct. 19, 2001.

(51) Int. Cl.
*A61K 31/404* (2006.01)
*C07D 403/14* (2006.01)
*C07D 405/14* (2006.01)

(52) U.S. Cl. .................................... 514/414; 548/455
(58) Field of Classification Search ............... 548/455; 514/414

See application file for complete search history.

(56) References Cited

U.S. PATENT DOCUMENTS

| 3,527,517 | A | | 9/1970 | Hackmann | |
| 3,995,088 | A | * | 11/1976 | Garner et al. | 428/323 |
| 4,072,690 | A | * | 2/1978 | Garner et al. | 260/326.14 |
| 4,403,791 | A | * | 9/1983 | Schmidt et al. | 282/27.5 |

FOREIGN PATENT DOCUMENTS

| EP | 0 887 348 A1 | 12/1998 |
| WO | WO 99/61435 | 12/1999 |
| WO | WO 01/16097 | 3/2001 |
| WO | WO 01/81307 A2 | 11/2001 |

OTHER PUBLICATIONS

Gray et al., CA 51:16466b, 1957.*
D'Auria, Tetrahedron (1991), 47(44), pp. 9225-9230.*
Dittmann et al., CA 103:22412, 1985.*
Bergman et al., CA 90:204315, 1979.*
Kramer et al., CA 86:199415, 1977.*
Novak et al., Journal of Organic Chemistry (1976), 41(5), pp. 870-875.*
Golub et al., Science, vol. 286, Oct. 15, 1999, pp. 531-537.*
Iversen, L.F., et al., Steric Hindrance as a Basis for Structure-Based Design of Selective Inhibitors of Protein-Tyrosine Phosphatases, Biochemistry, 2001, 40, No. 49, 14812-14820.
Bleasdale, J.E., et al., Small Molecule Peptidomimectics Containing a Novel Phosphotyrosine Bioisostere Inhibit Protein Tyrosine Phosphatase 1B and Augment Insulin Action, Biochemistry, 2001, 40, 5642-5654.
Shim, Y.S., et al., Formylchromone Derivatives as a Novel Class of Protein Tyrosine Phosphatase 1B Inhibitors, Bioorganic & Medicinal Chemistry Letters, 13, (2003) 2561-2563.
Cheon, H.G., et al., Discovery of a Novel Protein Tyrosine Phosphatase-1N Inhibitor, KR61639: Potential Development as an Antihyperglycemic Agent, European Journal of Pharmacology, 485 (2004) 333-339.
Urbanek, R.A., et al., Potent Reversible Inhibitors of Protein Tyrosine Phosphatase CD45, J. Med. Chem., 2001, 44, 1777-1793.
Umezawa, K., et al., Molecular Design and Biological Activities of Protein-Tyrosine Phosphatase Inhibitors, Pharmacology & Therapeutics, 99, (2003), 15-24.
Sarmiento, M., et al., Structure-Based Discovery of Small Molecule Inhibitors Targeted to Protein Tyrosine Phosphatase 1B, J. Med. Chem., 2000, 43, 146-155.

* cited by examiner

*Primary Examiner*—Laura L. Stockton
(74) *Attorney, Agent, or Firm*—Kilpatrick Stockton

(57) ABSTRACT

This invention provides compounds which are useful as inhibitors of protein tyrosine phosphatases (PTPases). As inhibitors of PTPases the compounds of the invention are useful for the management, treatment, control and adjunct treatment of diseases in mammals mediated by PTPase activity. Such diseases include type I diabetes, type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

16 Claims, No Drawings

BIS-HETEROARYL ALKANES AS THERAPEUTIC AGENTS

STATEMENT OF RELATED APPLICATION

The present application claims priority under 35 USC 119 from the following U.S. Provisional Application: Ser. No. 60/348,187, filed Oct. 19, 2001, entitled "Bis-Heteroaryl Alkanes as Therapeutic Agents," the entirety of which is herein incorporated by reference.

FIELD OF THE INVENTION

This invention relates to compounds which are inhibitors of protein tyrosine phosphatases (PTPases), which are useful for the management, treatment, control, or adjunct treatment of diseases caused by over-activity of PTPases.

BACKGROUND OF THE INVENTION

The process of protein phosphorylation is now recognized as central to the fundamental processes of cellular signal transduction. Alterations in protein phosphorylation, may therefore constitute either a physiological or pathological change in an in vivo system. Protein de-phosphorylation, mediated by phosphatases, is also central to certain signal transduction processes.

The two major classes of phosphatases are (a) protein serine/threonine phosphatases (PSTPases), which catalyze the dephosphorylation of serine and/or threonine residues on proteins or peptides; and (b) the protein tyrosine phosphatases (PTPases), which catalyze the dephosphorylation of tyrosine residues on proteins and/or peptides. A third class of phosphatases is the dual specificity phosphatases, or DSP's, which possess the ability to act both as PTPases and as PSTPases.

Among the PTPases there exist two important families, the intracellular PTPases, and the transmembrane PTPases. The intracellular PTPases include PTP1B, STEP, PTPD1, PTPD2, PTPMEG1, T-cell PTPase, PTPH1, FAP-1/BAS, PTP1D, and PTP1C. The transmembrane PTPases include LAR, CD45, PTPα, PTPβ, PTPδ, PTPε, PTPξ, PTPκ, PYPμ, PTPσ, HePTP, SAP-1, and PTP-U2. The dual—specificity phosphatases include KAP, cdc25, MAPK phosphatase, PAC-1, and rVH6.

The PTPases, especially PTP1B, are implicated in insulin insensitivity characteristic of type II diabetes (Kennedy, B. P.; Ramachandran, C. *Biochem. Pharm.* 2000, 60, 877–883). The PTPases, notably CD45 and HePTP, are also implicated in immune system function, and in particular T-cell function. Certain PTPases, notably TC-PTP, DEP-1, SAP-1, and CDC25, are also implicated in certain cancers. Certain PTPases, notably the bone PTPase OST-PTP, are implicated in osteoporosis. PTPases are implicated in mediating the actions of somatostatin on target cells, in particular the secretion of hormone and/or growth factor secretion.

Thus, there is a need for agents which inhibit the action of protein tyrosine phosphatases. Such agents would be useful for the treatment of type I diabetes, type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

SUMMARY OF THE INVENTION

This invention provides bis-heteroaryl alkanes which are useful as inhibitors of PTPases. In a preferred embodiment, the present invention provides compounds of Formula (I) as depicted below, to methods of their preparation, pharmaceutical compositions comprising the compounds and to their use in treating human or animal disorders. The compounds of the invention are useful as inhibitors of protein tyrosine phosphatases and thus are useful for the management, treatment, control and adjunct treatment of diseases in mammals mediated by PTPase activity. Such diseases include type I diabetes, type II diabetes, immune dysfunction, AIDS, autoimmunity, glucose intolerance, obesity, cancer, psoriasis, allergic diseases, infectious diseases, inflammatory diseases, diseases involving the modulated synthesis of growth hormone or the modulated synthesis of growth factors or cytokines which affect the production of growth hormone, or Alzheimer's disease.

DETAILED DESCRIPTION OF THE INVENTION

In a first aspect, the present invention provides bis-heteroaryl alkane inhibitors of protein tyrosine phosphatases (PTPases) which are useful for the management and treatment of disease caused by PTPases.

In a second aspect, the present invention provides compounds of Formula (I):

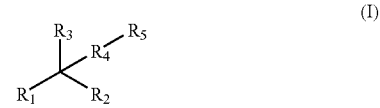

wherein
$R_1$ and $R_2$ independently comprise

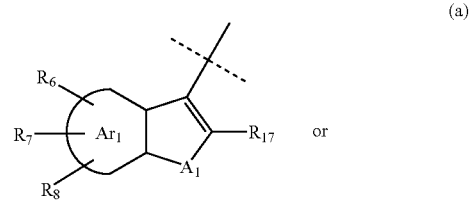

(a)

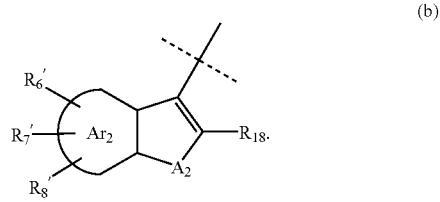

(b)

$R_3$ comprises
  (a) hydrogen;
  (b) alkyl;
  (c) alkenyl; or
  (d) alkynyl.
$R_4$ comprises
  (a) arylene; or
  (b) heteroarylene;

wherein $R_4$ is optionally substituted with a subsituent of the formula

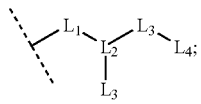

wherein
$L_1$ comprises a direct bond, alkylene, —O-alkylene-, alkylene-O—, —NH—C(O)—, —C(O)—NH— or —NH—CO—NH—;
$L_2$ comprisess alkyline, alkenyline, heteroaryline, aryline, or heterocyclyline;
$L_3$ comprises —O—, —C(O)—N($R_{19}$)—, —C(O)—O—, —C(O)—, or —N($R_{19}$)—CO—N($R_{20}$)—;
$L_4$ comprises hydrogen, alkyl, alkenyl, alkynyl, heterocyclyl, heteroaryl, or -alkylene-aryl;
$L_5$ comprises hydrogen, alkyl, alkenyl, alkynyl, -alkylene-aryl, -alkylene-heteroaryl, alkylene-O-alkylene-aryl, -alkylene-S-alkylene-aryl, -alkylene-O-alkyl, -alkylene-S-alkyl, -alkylene-NH$_2$, -alkylene-OH, -alkylene-SH, -alkylene-C(O)—OR$_9$, -alkylene-C(O)—NR$_9$R$_{10}$, -alkylene-NR$_9$R$_{10}$, -alkylene-N(R$_9$)—C(O)—R$_{10}$, or -alkylene-N(R$_9$)—S(O$_2$)—R$_{10}$;

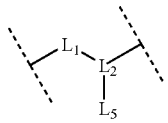

may be taken together to constitute a direct bond.
$R_5$ comprises
(a) hydrogen;
(b) alkyl;
(c) alkenyl;
(d) alkynyl;
(e) aryl;
(f) heteroaryl;
(g) cycloalkyl;
(h) heterocyclyl;
(i) alkylene-OH;
(j) alkylene-COOH;
(k) alkylene-NH$_2$;
(l) COOH;
(m) CONH$_2$; or
(n) NH$_2$.
$R_6$, $R_6'$, $R_7$, $R_7'$, $R_8$, and $R_8'$, independently, comprise
(a) hydrogen;
(b) aryl;
(c) heteroaryl;
(d) heterocyclyl;
(e) cycloalkyl; or
(f) -alkylene-Y-aryl; -alkenylene-Y-aryl; -alkynylene-Y-aryl; -alkylene-Y-heteroaryl; -alkenylene-Y-heteroaryl; -alkynlene-Y-heteroaryl; -alkylene-Y-cycloalkyl-alkenylene-Y-cycloalkyl; -alkynlene-Y-cycloalkyl; -alkylene-Y-heterocyclyl; -alkenylene-Y-heterocyclyl; -alkynlene-Y-heterocyclyl; —Y-alkyl; —Y-aryl; —Y-alkylene-aryl; —Y-alkylene-NR$_{11}$R$_{12}$; —Y—O—Si-(alkyl)$_3$; or —Y—O—Si-(alkylene-aryl)$_3$;

wherein Y comprises —CH$_2$—, —C(O)—, —O—, —N(H)—, —S—, —S(O)—, —S(O$_2$)—, —CON(H)—, —NHC(O)—, —NHCON(H)—, —NHS(O$_2$)—, —S(O$_2$)N(H)—, —C(O)—O—, —NHS(O$_2$)NH—, —O—CO—; and
$R_{11}$ and $R_{12}$ independently comprise hydrogen, aryl, alkyl, or alkylene-aryl;
wherein
$R_{11}$ and $R_{12}$ may be taken together to form a ring having the formula —(CH$_2$)$_q$-Q-(CH$_2$)$_r$— bonded to the nitrogen atom to which $R_{11}$ and $R_{12}$ are attached, wherein q and r are, independently, 1, 2, 3, or 4; Q is —CH$_2$—, —C(O)—, —O—, —N(H)—, —S—, —S(O)—, —SO$_2$—, —CON(H)—, —NHC(O)—, —NHCON(H)—, —NHSO$_2$—, —SO$_2$N(H)—, —(O)CO—, —NHSO$_2$NH—, —OC(O)—, —N(R$_{13}$)—, —N(C(O)R$_{13}$)—, —N(C(O)NHR$_{13}$)—, —N(SO$_2$NHR$_{13}$)—, —N(SO$_2$R$_{13}$)—, and —N(C(O)OR$_{13}$)—; or
$R_{11}$ and $R_{12}$ may be taken together, with the nitrogen atom to which they are attached, to form a heterocyclyl or heteroaryl ring.
$R_9$, $R_{10}$, $R_{13}$, $R_{19}$, and $R_{20}$ independently comprise hydrogen, aryl, alkyl, or alkylene-aryl. $A_1$ and $A_2$ independently comprise O, S, or N—R$_{14}$, where $R_{14}$ comprises
(a) hydrogen;
(b) alkyl; alkenyl; alkynyl;
(c) heterocyclyl; cycloalkyl;
(d)-alkylene-aryl; -alkenylene-aryl; -alkynylene-aryl; -alkyloxy-aryl; -alkylene-heteroaryl; -alkenylene-heteroaryl; -alkynylene-heteroaryl; -alkoxy-heteroaryl;
(e)-alkylene-heterocyclyl; -alkenylene-heterocyclyl; -alkynylene-heterocyclyl;
(f)-alkylene-C(O)—OR$_{16}$; -alkenylene-C(O)—OR$_{16}$; alkynylene-C(O)—OR$_{16}$; —C(O)—NR$_{16}$R$_{15}$; alkylene-C(O)—NR$_{16}$R$_{15}$; alkenylene-C(O)—NR$_{16}$R$_{15}$; alkynylene-C(O)— NR$_{16}$R$_{15}$; alkylene-O-aryl; alkylene-O-alkylene-aryl; alkylene-O-cycloalkyl; —S(O$_2$)—R$_{16}$; alkylene-S(O$_2$)—R$_{16}$; alkenylene-S(O$_2$)—R$_{16}$; alkynylene-S(O$_2$)—R$_{16}$; alkylene-S(O)—R$_{16}$; alkenylene-S(O)—R$_{16}$; alkynylene-S(O)—R$_{16}$; alkylene-S(O)—R$_{16}$; alkenylene-S(O)—R$_{16}$; alkynylene-S(O)—R$_{16}$; —S(O$_2$)—NR$_{16}$R$_{15}$; alkylene-S(O$_2$)—NR$_{16}$R$_{15}$; -alkenylene-S(O$_2$)—NR$_{16}$R$_{15}$; alkynylene-S(O$_2$)—NR$_{16}$R$_{15}$; wherein
$R_{16}$ and $R_{15}$ independently comprise hydrogen, aryl, alkyl, or alkylene-aryl;
wherein
$R_{16}$ and $R_{15}$ may be taken together to form a ring having the formula —(CH$_2$)$_x$-Z-(CH$_2$)$_y$— bonded to the nitrogen atom to which $R_{16}$ and $R_{15}$ are attached, wherein x and y are, independently, 1, 2, 3, or 4; Z is —CH$_2$—, —O—, —N(H)—, —S—, —S(O$_2$)—, —CON(H)— —NHC(O)—, —NHCON(H)—, —NHS(O$_2$)—, —S(O$_2$)N(H)—, —(O)CO—, —NHS(O$_2$)NH—, —OC(O)—, —N(R$_{21}$)—, —N(C(O)R$_{21}$)—, —N(C(O)NHR$_{21}$)—, —N(S)O$_2$)NHR$_{21}$)—, —N(SO$_2$R$_{21}$)—, and —N(C(O)OR$_{21}$)—; or
$R_{16}$ and $R_{15}$ may be taken together, with the nitrogen atom to which they are attached, to form a heterocyclyl or heteroaryl ring.
$R_{21}$ is selected from the group consisting of hydrogen, aryl, alkyl, or -alkylene-aryl.

$R_{17}$ and $R_{18}$ independently comprise, hydrogen, alkyl, or halogen.

$Ar_1$ and $Ar_2$ are, independently, aryl or heteroaryl.

The compound of Formula (I) may comprise a pharmaceutically acceptable salt, solvate or prodrug thereof.

In a preferred embodiment, $R_1$ and $R_2$ independently comprise indol-3-yl; 4-chloroindol-3-yl; 2-methylindol-3-yl; 6-chloroindol-3-yl; 5-benzyloxyindol-3-yl; 1-methylindol-3-yl; 4-chloro-1-methylindol-3-yl; 4-chloro-1-ethylindol-3-yl; 4-chloro-1-butylindol-3-yl; 4-chloro-1-benzylindol-3-yl; or 4-chloro-1-benzylindol-3-yl.

In another preferred embodiment, $R_4$ in combination with $R_5$ comprise 5-carboxy-2-furyl; 1,1'-biphenyl-4-yl; 5-hydroxymethylfuran-2-yl; 4-fluoro-2-trifluoromethyl 2,4-difluorophenyl; 4-fluoro-2-chlorophenyl; 2,4-dichlorophenyl; 5-hydroxymethyl-2-furyl; 2-chloro-4-fluorophenyl; 2-chloro-4-fluorophenyl; or 5-methoxycarbonylmethoxymethyl-2-furyl.

In another preferred embodiment, $R_1$ and $R_2$ independently comprise indol-3-yl, 1-methylindol-3-yl or 4-chloro-1-ethylindol-3-yl; $R_3$ comprises ethyl, methyl or hydrogen; $R_4$ comprises phenylene or 2-furan-5-yl; and $R_5$ comprises hydrogen or —CH$_2$—OH.

In another preferred embodiment, $R_6$, $R_6'$, $R_7$, $R_7'$, $R_8$, and $R_8'$, independently, comprise a hydrogen, halogen, alkyl, or —O-alkylene-phenyl group.

In a more preferred embodiment, $R_1$ and $R_2$ independently comprise indol-3-yl, 4-chloroindol-3-yl, 2-methylindol-3-yl; 6-chloroindol-3-yl, 5-benzyloxyindol-3-yl, 1-methylindol-3-yl, 4-chloro-1-methylindol-3-yl; 4-chloro-1-ethylindol-3-yl, 4-chloro-1-butylindol-3-yl, 4-chloro-1-benzylindol-3-yl, or 4-chloro-1-benzylindol-3-yl; $R_4$ in combination with $R_5$ comprise 5-carboxy-2-furyl, 1,1'-biphenyl-4-yl, 5-hydroxymethylfuran-2-yl, 4-fluoro-2-trifluoromethylphenyl, 2,4-difluorophenyl, 4-fluoro-2-chlorophenyl, 2,4-dichlorophenyl, 5-hydroxymethyl-2-furyl, 2-chloro-4-fluorophenyl, 2-chloro-4-fluorophenyl, or 5-methoxycarbonylmethoxymethyl-2-furyl.

Compounds of the present invention which are currently preferred for their biological activity are listed by name below in Table 1.

The potential ability of compounds of Formula (I) to treat or inhibit disorders related to insulin resistance or hyperglycemia was established with representative compounds of Formula (I) in the following standard primary/secondary assay test procedure which measures the inhibition of PTP-1B activity.

The compounds of this invention are potentially useful in treating metabolic disorders related to insulin resistance or hyperglycemia, typically associated with obesity or glucose intolerance. The compounds of this invention, therefore, should prove particularly useful in the treatment or inhibition of type II diabetes. The compounds of this invention are also potentially useful in modulating glucose levels in disorders such as type I diabetes.

The potential ability of compounds Formula (I) to treat or inhibit disorders related to insulin resistance or hyperglycemia was also established with representative compounds of Formula (I) in the following standard primary/secondary assay test procedure which measures the inhibition of PTPase.

TABLE 1

| Example | Structure | Name |
|---------|-----------|------|
| 1 | 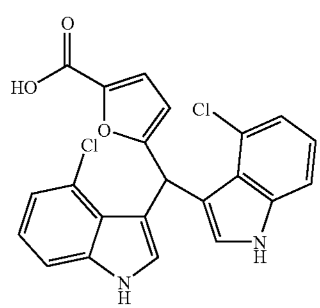 | Bis(4-chloroindol-3-yl)-(5-carboxy-2-furyl)methane |
| 2 | 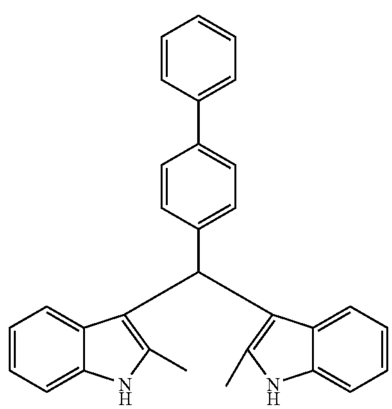 | Bis(2-methylindol-3-yl)-(1,1'-biphenyl-4-yl)methane |

TABLE 1-continued

| Example | Structure | Name |
|---|---|---|
| 3 | 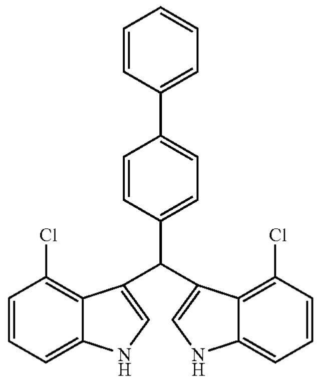 | Bis(4-chloroindol-3-yl)-(1,1'-biphenyl-4-yl)methane |
| 4 | 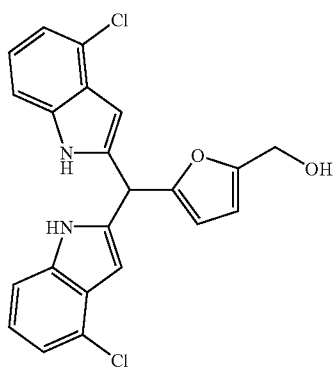 | Bis(4-chloroindol-3-yl)-(5-hydroxymethylfuran-2-yl)methane |
| 5 | 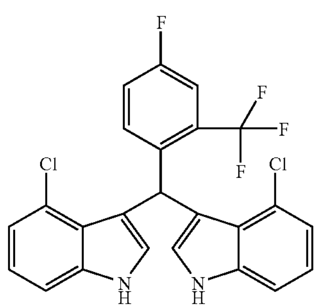 | Bis(4-chloroindol-3-yl)-(4-fluoro-2-trifluoromethylphenyl)methane |
| 6 | 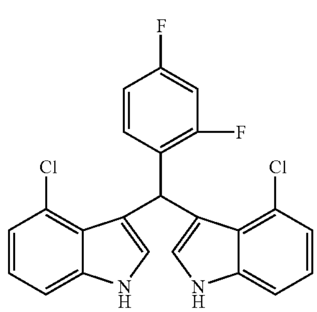 | Bis(4-chloroindol-3-yl)-(2,4-difluorophenyl)methane |

TABLE 1-continued

| Example | Structure | Name |
|---|---|---|
| 7 | 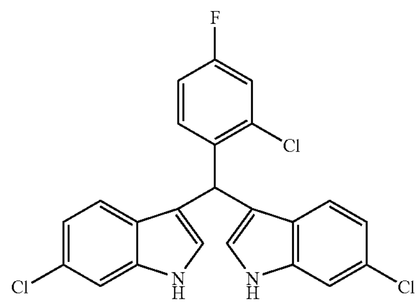 | Bis(6-chloroindol-3-yl)-(4-fluoro-2-chlorophenyl)methane |
| 8 | 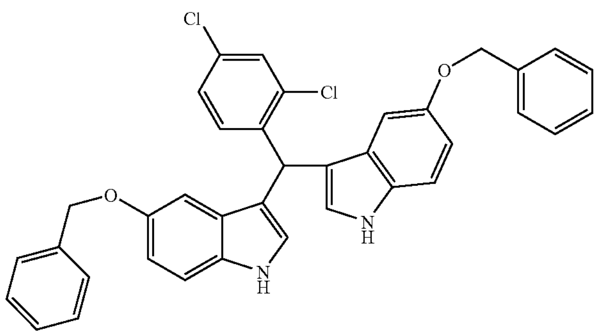 | Bis(5-benzyloxyindol-3-yl)-(2,4-dichlorophenyl)methane |
| 9 | 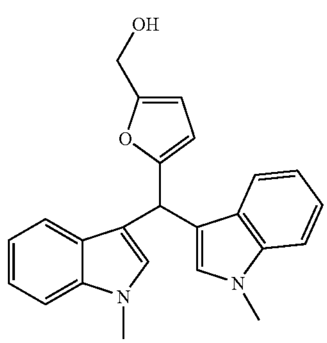 | Bis(1-methylindol-3-yl)-(5-hydroxymethyl-2-furyl)methane |
| 10 | 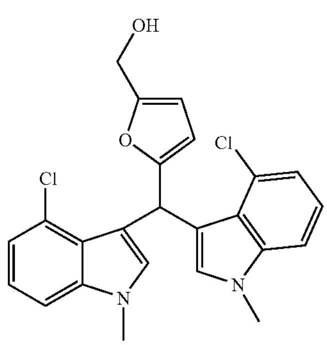 | Bis(4-chloro-1-methylindol-3-yl)-(5-hydroxymethyl-2-furyl)methane |

TABLE 1-continued

| Example | Structure | Name |
|---|---|---|
| 11 | 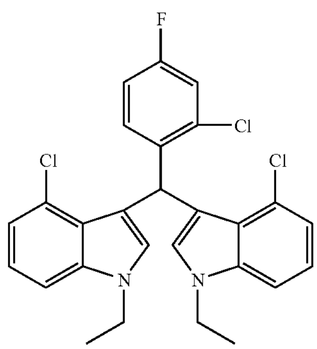 | Bis(4-chloro-1-ethylindol-3-yl)-(2-chloro-4-fluorophenyl)methane |
| 12 | 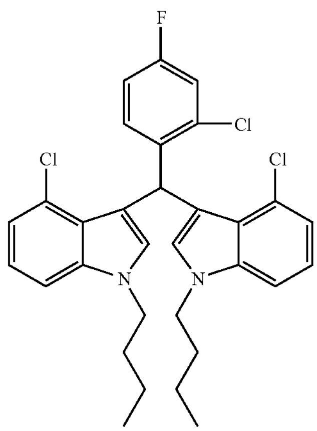 | Bis(4-chloro-1-butylindol-3-yl)-(2-chloro-4-fluorophenyl)methane |
| 13 | 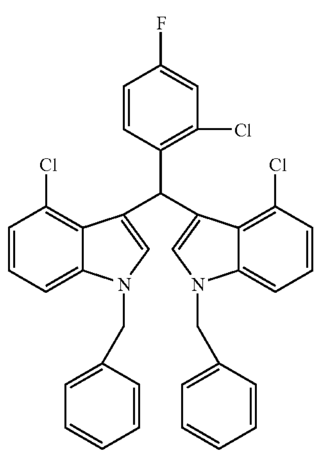 | Bis(4-chloro-1-benzylindol-3-yl)-(2-chloro-4-fluorophenyl)methane |
| 14 | 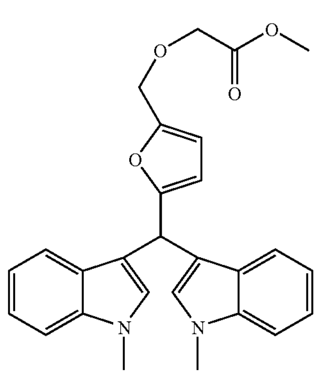 | Bis(1-methylindol-3-yl)-(5-methoxycarbonylmethoxymethyl-2-furyl)methane |

TABLE 1-continued

| Example | Structure | Name |
|---|---|---|
| 15 | 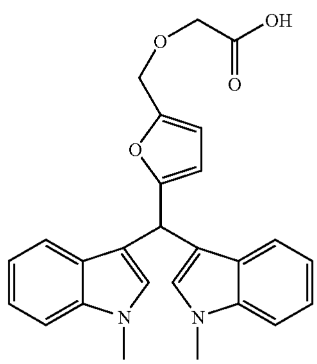 | Bis(1-methylindol-3-yl)-(5-carboxymethoxymethyl-2-furyl)methane |
| 16 | 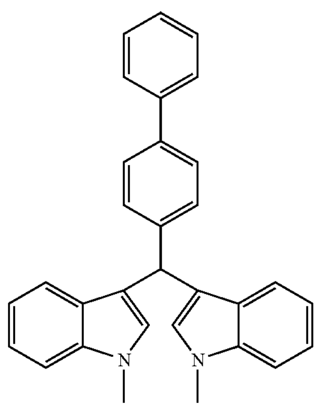 | Bis(1-methylindol-3-yl)-(1,1'-biphenyl-4-yl)methane |
| 17 | 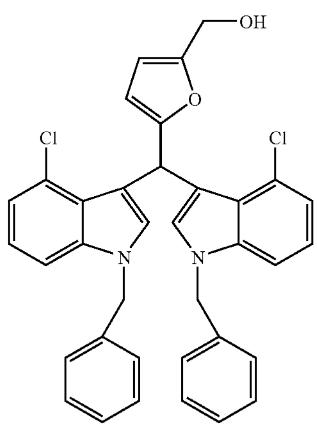 | Bis(4-chloro-1-benzylindol-3-yl)-(5-hydroxymethyl-2-furyl)methane |

In the compounds of Formula (I), the various functional groups represented should be understood to have a point of attachment at the functional group having the hyphen. In other words, in the case of -alkylene-aryl, it should be understood that the point of attachment is the alkylene group; an example would be benzyl. In the case of a group such as —C(O)—NH— alkylene-aryl, the point of attachment is the carbonyl carbon.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

In another aspect, the present invention comprises a pharmaceutical composition comprising the compound of Formula (i) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkyl" as used herein include, but are not limited to, methyl, n-butyl, n-pentyl, isobutyl, and isopropyl, and the like. As used herein, the term "lower" refers to a group having between one and six carbons.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkylene" as used herein include, but are not limited to, methylene, ethylene, and the like.

As used herein, the term "alkyline" refers to a straight or branched chain trivalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkyline" as used herein include, but are not limited to, methine, ethyline, and the like.

As used herein, the term "alkenyl" refers to a hydrocarbon radical having from two to ten carbons and at least one carbon—carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

As used herein, the term "alkenylene" refers to a straight or branched chain divalent hydrocarbon radical having from two to ten carbon atoms and one or more carbon—carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkenyline" refers to a straight or branched chain triivalent hydrocarbon radical having from two to ten carbon atoms and one or more carbon—carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkenyline" as used herein include, but are not limited to, ethene-1,1,2-triyl, propene-1,2,3-triyl, and the like.

As used herein, the term "alkynyl" refers to a hydrocarbon radical having from two to ten carbons and at least one carbon—carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon—carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group optionally with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "heterocyclyline" refers to a three to twelve-membered heterocyclic ring triradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclyline" include, but are not limited to, tetrahydrofuran-2,4,5-triyl, morpholine-2,3,4-triyl, pyran-2,4,5-triyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower hydroxyalkyl, lower carboxyalkyl, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "aryline" refers to a benzene ring triradical or to a benzene ring system triradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "aryline" include, but are not limited to, benzene-1,2,4-triyl, naphthalene-1,4,8-triyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, lower hydroxyalkyl, lower carboxyalkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "heteroaryline" refers to a five- to seven-membered aromatic ring triradical, or to a polycyclic heterocyclic aromatic ring triradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroaryline" used herein are furan-2,4,5-triyl, thiophene-2,3,4-triyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

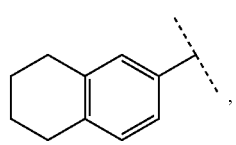

and the like.

As used herein, the term "fused cycloalkylarylene" refers to a fused cycloalkylaryl, wherein the aryl group is divalent. Examples include

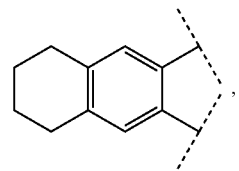

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

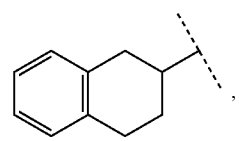

and the like.

As used herein, the term "fused arylcycloalkylene" refers to a fused arylcycloalkyl, wherein the cycloalkyl group is divalent. Examples include

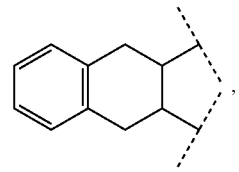

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

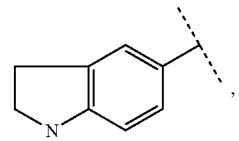

and the like

As used herein, the term "fused heterocyclylarylene" refers to a fused heterocyclylaryl, wherein the aryl group is divalent. Examples include

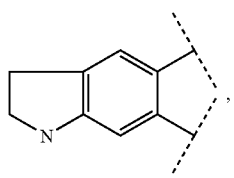

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

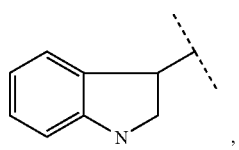

and the like.

As used herein, the term "fused arylheterocyclylene" refers to a fused arylheterocyclyl, wherein the heterocyclyl group is divalent. Examples include

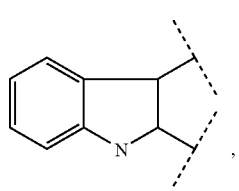

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

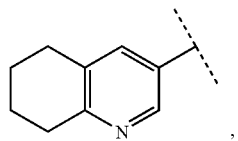

and the like.

As used herein, the term "fused cycloalkylheteroarylene" refers to a fused cycloalkylheteroaryl, wherein the heteroaryl group is divalent. Examples include

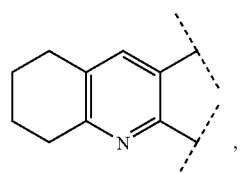

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

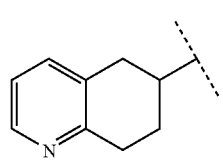

and the like.

As used herein, the term "fused heteroarylcycloalkylene" refers to a fused heteroarylcycloalkyl, wherein the cycloalkyl group is divalent. Examples include

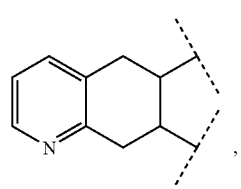

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

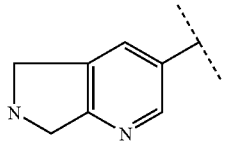

and the like.

As used herein, the term "fused heterocyclylheteroarylene" refers to a fused heterocyclylheteroaryl, wherein the heteroaryl group is divalent. Examples include

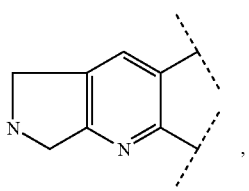

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

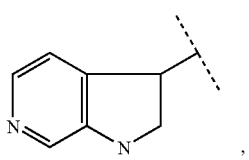

and the like.

As used herein, the term "fused heteroarylheterocyclylene" refers to a fused heteroarylheterocyclyl, wherein the heterocyclyl group is divalent. Examples include

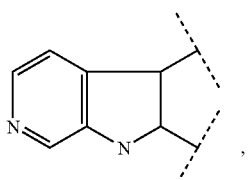

and the like.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO$—, where $R_a$ is alkyl.

As used herein, the term "alkenyloxy" refers to the group $R_bO$—, where $R_b$ is alkenyl.

As used herein, the term "alkynyloxy" refers to the group $R_cO$—, where $R_c$ is alkynyl.

As used herein, the term "alkylsulfanyl" refers to the group $R_aS$—, where $R_a$ is alkyl.

As used herein, the term "alkenylsulfanyl" refers to the group $R_bS$—, where $R_b$ is alkenyl.

As used herein, the term "alkynylsulfanyl" refers to the group $R_cS$—, where $R_c$ is alkynyl.

As used herein, the term "alkylsulfenyl" refers to the group $R_aS(O)$—, where $R_a$ is alkyl.

As used herein, the term "alkenylsulfenyl" refers to the group $R_bS(O)$—, where $R_b$ is alkenyl.

As used herein, the term "alkynylsulfenyl" refers to the group $R_cS(O)$—, where $R_c$ is alkynyl.

As used herein, the term "alkylsulfonyl" refers to the group $R_aSO_2$—, where $R_a$ is alkyl.

As used herein, the term "alkenylsulfonyl" refers to the group $R_bSO_2$—, where $R_b$ is alkenyl.

As used herein, the term "alkynylsulfonyl" refers to the group $R_cSO_2$—, where $R_c$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_1$–$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of Formula (I): for example, the lactam formed by a carboxylic group in $R_2$ and an amine in $R_4$, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" or "treating" as used herein, refers to the full spectrum of treatments for a given disorder from which the patient is suffering, including alleviation of one, most of all symptoms resulting from that disorder, to an outright cure for the particular disorder or prevention of the onset of the disorder.

The present invention also provides a method for the synthesis of compounds useful as intermediates in the preparation of compounds of Formula (I) along with methods for the preparation of compounds of Formula (I). The compounds can be prepared readily according to the following reaction Schemes (in which all variables are as defined before) using readily available starting materials, reagents and conventional synthetic procedures. In these reactions, it is also possible to make use of variants which are themselves known to those of ordinary skill in this art, but are not mentioned in greater detail.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N, N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral PBS=phosphate buffered saline solution
PMA=phorbol myristate acetate
ppm=parts per million
psi=pounds per square inch
$R_f$=relative TLC mobility
rt=room temperature
s.c=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time Unless otherwise specified, the variables in the Schemes are as defined for Formula (I).

The carbonyl compound (3) (Scheme 1) may be treated with two molar equivalents of heteroaryl species, here represented by compounds (1) and (2) & (both are similar also). The reaction may be catalyzed by a Lewis acid such as, but not limited to, $Yb(OS(O_2)CF_3)_3$ or $BF_3$ in a solvent such as dichloromethane, toluene, ethanol, or methanol, to afford the bis-adduct (4). The reaction may be conducted at temperatures of from −20° C. to 110° C.

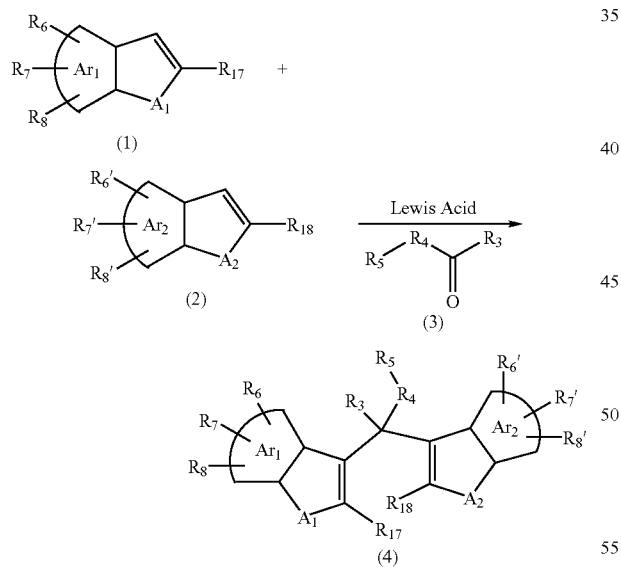

Scheme 1

In another embodiment, indole nitrogen in compound (4) (Scheme 2) may be alkylated with alkyl halides or aryl-alkyl halides such as, but not limited to, $Br-(CH_2)_f-R_{40}$ wherein f ranges from 1 to 6, in the presence of base such as, but not limited to, sodium hydride, potassium tert-butoxide, or potassium carbonate using DMF, THF, acetonitrile as the solvent at temperatures ranging from 0° C. to 80° C. to afford N-alkylated products (5). $R_{40}$ may be a group such as, but not limited to, alkyl, aryl, or heteroaryl.

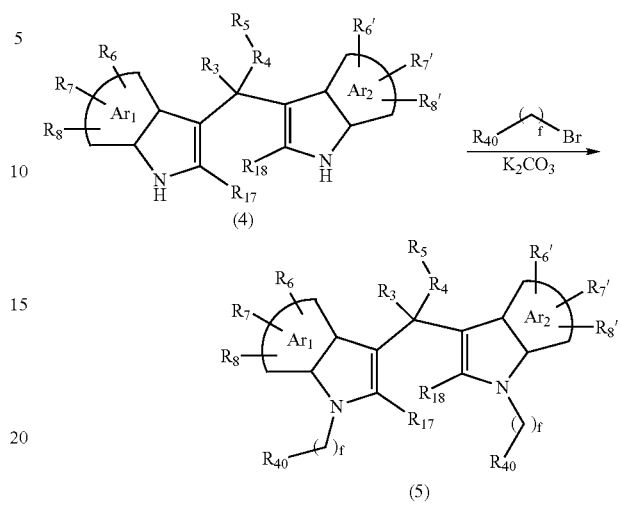

Scheme 2

In another embodiment, the alcohols (6)(Scheme 3) may be alkylated with bromo or chloro alkyl carboxylates such as, but not limited to, $Br-(CH_2)_g CO_2R_{41}$ wherein g ranges from 1 to 6, in the presence of base such as, but not limited to, sodium hydride, potassium tert-butoxide, potassium carbonate using DMF, THF, acetonitrile as the solvent at temperatures ranging from 50° C. to 100° C. to afford branched esters (7). Subsequent saponification of esters (7) with base such, but not limited to, as sodium hydroxide, lithium hydroxide in aqueous and organic solvents such as THF, methanol, at temperatures ranging from room temperature to 60° C. may be used to produce carboxylic acid (8), where $Ar_1$, $R_1$–$R_{18}$ are defined in formula. $R_{41}$ may be a group such as, but not limited to, alkyl, -alkyl-aryl, or cycloalkyl. $R_{42}$ may be a group such as, but not limited to, arylene, arylene-alkylene, heteroarylene-alkylene, or heteroarylene.

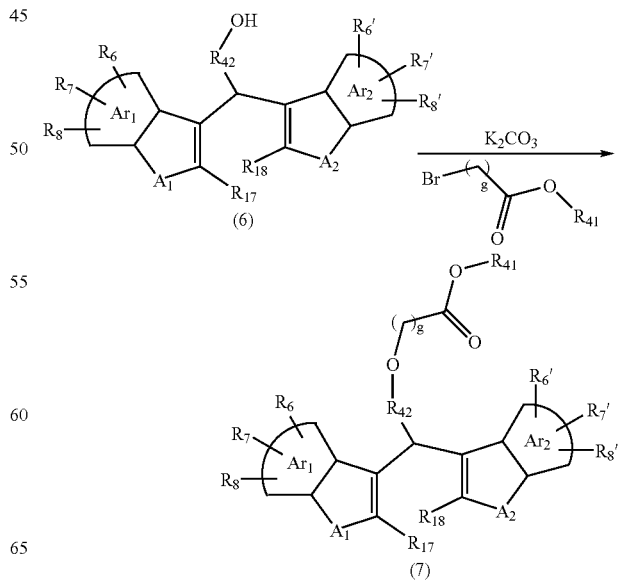

Scheme 3

-continued

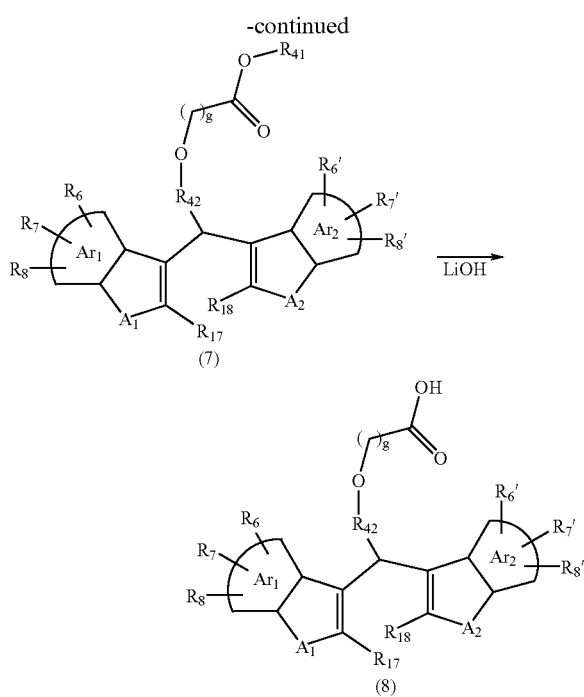

The compounds of the present invention are inhibitors of protein tyrosine phosphatases (PTPases). The invention described herein is additionally directed to pharmaceutical compositions and methods of inhibiting PTPase activity in a mammal, which methods comprise administering, to a mammal in need of inhibition of PTPase activity, a therapeutically defined amount of a compound of formula (1), defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

Thus, the present invention provides a method of inhibiting a PTPase, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit a PTPase. A PTPase-inhibiting amount can be an amount that reduces or inhibits a PTPase activity in the subject.

Additionally provided is a pharmaceutical composition comprising a pharmaceutically acceptable carrier and a pharmacologically effective amount of a compound of the present invention sufficient to treat type I diabetes.

Further, the present invention provides a pharmaceutical composition comprising a pharmaceutically acceptable carrier and a pharmacologically effective amount of a compound of the present invention sufficient to treat type II diabetes.

Further, the present invention provides a pharmaceutical composition comprising a pharmaceutically acceptable carrier and a pharmacologically effective amount of a compound of the present invention sufficient to treat immune dysfunction.

Further, the present invention provides a pharmaceutical composition comprising a pharmaceutically acceptable carrier and a pharmacologically effective amount of a compound of the present invention sufficient to treat AIDS.

Further, the present invention provides a pharmaceutical composition comprising a pharmaceutically acceptable carrier and a pharmacologically effective amount of a compound of the present invention sufficient to treat autoimmune diseases Further, the present invention provides a pharmaceutical composition comprising a pharmaceutically acceptable carrier and a pharmacologically effective amount of a compound of the present invention sufficient to treat glucose intolerance.

Further, the present invention provides a pharmaceutical composition comprising a pharmaceutically acceptable carrier and a pharmacologically effective amount of a compound of the present invention sufficient to treat obesity.

Further, the present invention provides a pharmaceutical composition comprising a pharmaceutically acceptable carrier and a pharmacologically effective amount of a compound of the present invention sufficient to treat cancer.

Further, the present invention provides a pharmaceutical composition comprising a pharmaceutically acceptable carrier and a pharmacologically effective amount of a compound of the present invention sufficient to treat psoriasis.

Further, the present invention provides a pharmaceutical composition comprising a pharmaceutically acceptable carrier and a pharmacologically effective amount of a compound of the present invention sufficient to treat allergic diseases Further, the present invention provides a pharmaceutical composition comprising a pharmaceutically acceptable carrier and a pharmacologically effective amount of a compound of the present invention sufficient to treat infectious diseases.

Further, the present invention provides a pharmaceutical composition comprising a pharmaceutically acceptable carrier and a pharmacologically effective amount of a compound of the present invention sufficient to treat inflammatory diseases.

Further, the present invention provides a pharmaceutical composition comprising a pharmaceutically acceptable carrier and a pharmacologically effective amount of a compound of the present invention sufficient to treat diseases involving the modulated synthesis of growth hormone.

Further, the present invention provides a pharmaceutical composition comprising a pharmaceutically acceptable carrier and a pharmacologically effective amount of a compound of the present invention sufficient to treat diseases involving the modulated synthesis of growth factors or cytokines which affect the production of growth hormone.

Further, the present invention provides a pharmaceutical composition comprising a pharmaceutically acceptable carrier and a pharmacologically effective amount of a compound of the present invention sufficient to treat Alzheimer's disease.

The compounds of the present invention can be administered to subjects in need of inhibition of PTPase activity. Such subjects can include, for example, horses, cows, sheep, pigs, mice, dogs, cats, primates such as chimpanzees, gorillas, rhesus monkeys, and, most preferably humans.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadeca-ethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention. Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1–19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug therof, and one or more pharmaceutically acceptable carriers, excipients, or diluents.

The compounds of the present invention selectively act as inhibitors of one PTPase in preference to one or more other PTPases, and therefore may possess advantage in the treatment of one or more PTPase-mediated disease in preference to others.

Thus, in a further aspect, the present invention provides a method for the inhibition of PTPases. In a preferred embodiment of this aspect, the present invention provides a method for treating a disease states including diabetes, cancer, inflammation, Alzheimer's disease, psoriasis, or graft versus host disease, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of PTPase-mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (i).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

The following is a non-exhaustive listing of adjuvants and additional therapeutic agents which may be utilized in combination with the PTPase inhibitors of the present invention:

Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic classifications of treatment for Diabetes Mellitus
1. Sulfonylureas: Tolbutamide, Tolazamide, Glyburide, Glipizide
2. Biguamides: Metformin
3. Miscellaneous oral agents: Acarbose, Troglitazone, Rosiglitazone, Pioglitazone
4. Insulin Pharmacologic classifications of treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further preferred embodiment, the present invention provides a method of treating PTPase mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguamides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguamides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5%acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer.

Procedure A: Formation of Bis-Heteroaryl Adducts 1 equivalent of the desired aromatic aldehyde and 2 equivalents of desired heteroaryl compound was taken in 8:2 ratio of ethanol and water (0.1–0.5 M). The reaction mixture is heated at 80° C. for 6–12 hours and diluted with water and the layers are separated. The aqueous layer is further extracted with EtOAc, the organic layers combined, washed with brine, and the organic layer dried over sodium sulfate. The solvent is removed in vacuo, and the crude product purified by flash chromatography on silica gel to give the final product.

Procedure B: Alkylation of Nitrogen N—H Group

To a solution of compound (1 equivalent) in anhydrous DMF (0.8–1.5 M) is added freshly ground $K_2CO_3$ (1.5 equivalents), followed by an alkyl or aryl halide (1.1 equivalents). The reaction mixture is stirred at 80° C. for 2–6 hours, and then it was diluted with water/EtOAc and the layers separated. The aqueous layer is further extracted with EtOAc and the organic layers combined and dried over $Na_2SO_4$. The solvent was removed in vacuo and the residue is purified by silica gel chromatography to yield the final product.

Procedure C: O-Alkylation

To a solution of compound (1 equivalent) in anhydrous DMF (0.8–1.5 M) is added freshly ground $K_2CO_3$ (1.5 equivalents), followed by an alkyl or aryl halide (1.1 equivalents). The reaction mixture is stirred at 80° C. for 2–6 hours, and then it is diluted with water/EtOAc and the layers separated. The aqueous layer is further extracted with EtOAc and the organic layers combined and dried over $Na_2SO_4$. The solvent is removed in vacuo and the residue is purified by silica gel chromatography to yield the final product.

Procedure D: Hydrolysis of Methyl Ester

The methyl ester (1 equivalent) is suspended in a mixture of MeOH:THF:$H_2O$ (1:1:1; 0.1–0.2 M). LiOH (10–15 eq) was added and the mixture stirred at 40° C. for 3 hours. The solution is acidified with 10% citric acid, and extracted with ethyl acetate. The organic extracts are combined, washed with brine, dried over $Na_2SO_4$, and the solvent removed in vacuo. The residue is purified by silica gel chromatography to yield the final compound.

EXAMPLES

Example 1

The compound Bis(4-chloroindol-3-yl)-(5-carboxy-2-furyl)methane was prepared following procedure A, starting from 4-chloro indole and 5-formyl 2-furan carboxylic acid. LC: $T_r$ 2.31 min, MS: 425 $(M+H)^+$ Example 2

The compound Bis(2-methylindol-3-yl)-(1,1'-biphenyl-4-yl)methane was prepared following procedure A, starting from 2-methyl indole and 4-biphenyl carboxaldehyde. LC: $T_r$ 2.71 min, MS: 427 $(M+H)^+$ Example 3

The compound Bis(4-chloroindol-3-yl)-(1,1'-biphenyl-4-yl)methane was prepared following general procedure A, starting from 4-chloro indole and 4-biphenyl carboxaldehyde. LC: $T_r$ 2.79 min, MS: 467 $(M+H)^+$ Example 4

The compound Bis(4-chloroindol-3-yl)-(5-hydroxymethylfuran-2-yl)methane was prepared following procedure A, starting from 4-chloro indole and 5-hydroxymethyl furfural. LC: $T_r$ 2.84 min, MS: 411 $(M+H)^+$ Example 5

The compound Bis(4-chloroindol-3-yl)-(4-fluoro-2-trifluoromethylphenyl)methane was prepared following procedure A, starting from 4-chloro indole and 4-fluoro-2-(trifluromethyl) benzaldehyde. LC: $T_r$ 2.52 min, MS: 477 $(M+H)^+$ Example 6

The compound Bis(4-chloroindol-3-yl)-(2,4-difluorophenyl)methane was prepared following procedure A, starting from 4-chloro indole and 2,4-difluoro benzaldehyde. LC: $T_r$ 2.63 min, MS: 427 $(M+H)^+$ Example 7

The compound Bis(6-chloroindol-3-yl)-(4-fluoro-2-chlorophenyl)methane was prepared following procedure A, starting from 6-chloro indole and 2-chloro 4-fluoro benzaldehyde. LC: $T_r$ 2.79 min, MS: 443 $(M+H)^+$ Example 8

The compound Bis(5-benzyloxyindol-3-yl)-(2,4-dichlorophenyl)methane was prepared following procedure A, starting from 5-benzyloxy indole and 2,4 dichloro benzaldehyde. LC: $T_r$ 2.89 min, MS: 603 (M+H)$^+$ Example 9

The compound Bis(1-methylindol-3-yl)-(5-hydroxymethyl-2-furyl)methane was prepared following general procedure A, starting from N-methyl indole and 5-hydroxy methyl furfural. LC: $T_r$ 2.25 min, MS: 371 (M+H)$^+$ Example 10

The compound Bis(4-chloro-1-methylindol-3-yl)-(5-hydroxymethyl-2-furyl)methane was prepared following procedure A, starting from N-methyl 4-chloro indole and 5-hydroxy methyl furfural. LC: $T_r$ 2.73 min, MS: 439 (M+H)$^+$ Example 11

The compound Bis(4-chloro-1-ethylindol-3-yl)-(2-chloro-4-fluorophenyl)methane was prepared following procedure A, starting from 4-chloro indole and 2-chloro 4-fluoro benzaldehyde, and the resulting compound was reacted with iodoethane following procedure B. LC: $T_r$ 2.83 min, MS: 499 (M+H)$^+$ Example 12

The compound Bis(4-chloro-1-butylindol-3-yl)-(2-chloro-4-fluorophenyl)methane was prepared following procedure A, starting from 4-chloro indole and 2-chloro 4-fluorobenzaldehyde, and the resulting compound was reacted with 1-bromobutane following procedure B. LC: $T_r$ 2.83 min, MS: 555 (M+H)$^+$ Example 13

The compound Bis(4-chloro-1-benzylindol-3-yl)-(2-chloro-4-fluorophenyl)methane was prepared following procedure A, starting from 4-chloro indole and 2-chloro 4-fluorobenzaldehyde, resulted compound was reacted with benzyl bromide following procedure B. LC: $T_r$ 2.94 min, MS: 623 (M+H)$^+$ Example 14

The compound Bis(1-methylindol-3-yl)-(5-methoxycarbonylmethoxymethyl-2-furyl)methane was prepared following procedure A, starting from N-methyl indole and 5-hydroxy methyl furfural, and the resulting compound was reacted with methyl bromo acetate following procedure C. LC: $T_r$ 2.47 min, MS: 443 (M+H)$^+$ Example 15

The compound Bis(1-methylindol-3-yl)-(5-carboxymethoxymethyl-2-furyl)methane was prepared from example 14 following procedure D. LC: $T_r$ 2.28 min, MS: 429 (M+H)$^+$ Example 16

The compound Bis(1-methylindol-3-yl)-(1,1'-biphenyl-4-yl)methane was prepared following procedure A, starting from N-methyl indole and 4-biphenyl carboxaldehyde. LC: $T_r$ 2.92 min, MS: 427 (M+H)$^+$ Example 17

The compound Bis(4-chloro-1-benzylindol-3-yl)-(5-hydroxymethyl-2-furyl)methane was prepared following procedure B, starting from 4-chloro indole and benzylbromide, and the resulting compound was reacted with 5-hydroxy methyl furfural following general procedure A. LC: $T_r$ 2.89 min, MS: 591 (M+H)$^+$ Example 18

The following assay methods are utilized to identify the effectiveness of compounds of Formula (I) in inhibiting the activity of certain phosphatases, examples of which, as used herein, are PTP1B and TC-PTP.

PTP1B Assay

The assay for PTP1B inhibition is based on the detection of the complex between Malachite Green dye and free phosphate, liberated from the phosphopeptide substrate by PTPase action. To each well of a flat-bottom assay plate is added 45 µL assay buffer [~50 mM Imidazole, pH 7.2, 100 mM NaCl, 5 mM DTT, and 1 mM EDTA] and 10 µL of peptide substrate [Tyrosine Phosphopeptide-1, END($_p$Y) INASL, 80 µM FAC, Promega Cat # V256A] to a total volume of 55 µL. Test compound (10 µL in up to 50% DMSO) is then added. The mixture is incubated for 5 min, at 25° C., and 10 µL of PTP-1B [Protein Tyrosine Phosphatase 1B (PTP-1B); FAC 0.8 nM; Upstate Biotechnology, Cat # 14–109 lot # 19045] is then added. The mixture is incubated for 30 min at 25° C. Subsequently, 25 µL of Malachite Green reagent [10% (w/v) Ammonium Molybdate in water, Sigma Cat # A-7302, 0.2% (w/v) Malachite Green in 4 N HCl, Aldrich Cat # 21,302-0] is then added. After incubation for 15 min at 27° C., the reaction endpoint is measured at 640 nM.

The Malachite Green reagent is prepared by mixing one volume of 10% Ammonium Molybdate with 3 volumes of 0.2% Malachite Green solution, stirring at room temperature for 30 min and then filtering and collecting the filtrate. The Malachite Green reagent is treated with 10 µL of 5% Tween 20 per 990 µL of dye solution before use.

T-Cell PTPase Assay

The assay for T-Cell PTPase (TC-PTP) inhibition is based on the detection of the complex between Malachite Green dye and free phosphate, liberated from the phosphopeptide substrate by PTPase action. To each well of a flat-bottom assay plate is added 45 µL assay buffer [~50 mM Imidazole, pH 7.2, 100 mM NaCl, 5 mM DTT, and 1 mM EDTA] and 10 µL of peptide [Tyrosine Phosphopeptide-1, END ($_p$Y) INASL at $k_m$=80 µM FAC; Promega Cat # V256A] to a total volume of 55 µL. The test compound (10 µL in up to 50% DMSO) is then added. The mixture is incubated for 5 min at 25° C., and 10 µL of 1 nM T-cell PTPase (CalBiochem) is then added. The mixture is incubated for an additional 30 min at 25° C. Subsequently, 25 µL of Malachite Green reagent [10% (w/v) Ammonium Molybdate in water; Sigma Cat # A-7302; 0.2% (w/v) Malachite Green in 4 N HCl; Aldrich Cat # 21,302-0] is then added. After incubation for 15 min at 27° C., the reaction endpoint is read at 640 nM.

The Malachite Green reagent is prepared by mixing one volume of 10% Ammonium Molybdate with 3 volumes of 0.2% Malachite Green solution, stirring at room temperature for 30 min and then filtering. The Malachite Green reagent is treated with 10 µL of 5% Tween 20 per 990 µL of dye solution before use.

Test compounds are typically examined at six concentrations in the above assay. For this assay, the $IC_{50}$ (microM) of the enzyme inhibition assay represents the concentration of compound at which 50% signal has been inhibited.

The compounds of the present invention are found to inhibit protein tyrosine phosphatase activity with inhibitory potencies of about 0.01 microM to about 30 microM. In a preferred range, the compounds inhibited protein tyrosine phosphatase activity with inhibitory potencies in a range of about 1 microM to about 10 microM. In a more preferred range, the compounds inhibited protein tyrosine phosphatase activity with inhibitory potencies of about 0.05 microM to about 3 microM.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for PTPase-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

What is claimed is:

1. A compound of Formula (I):

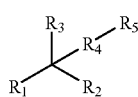

wherein $R_1$ and $R_2$ are independently selected from the group consisting of (a)

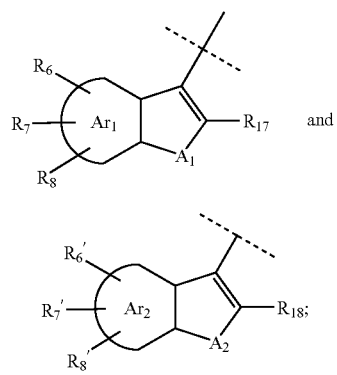

and b)

$R_3$ is
(a) hydrogen;
(b) alkyl;
(c) alkenyl; or
(d) alkynyl;

$R_4$ in combination with $R_5$ is: 5-carboxy-2-furyl; 5-hydroxymethylfuran-2-yl; or 5-methoxycarbonyl-methoxymethyl-2-furyl;

$R_6$, $R_6'$, $R_7$, $R_7'$, $R_8$, and $R_8'$ are independently selected from the group consisting of
(a) hydrogen;
(b) aryl;
(c) heteroaryl;
(d) heterocyclyl;
(e) cycloalkyl;
(f) halogen; and
(g) -alkylene-Y-aryl; -alkenylene-Y-aryl; -alkynylene-Y-aryl; -alkylene-Y-heteroaryl; -alkenylene-Y-heteroaryl; -alkynlene-Y-heteroaryl; -alkylene-Y-cycloalkyl -alkenylene-Y-cycloalkyl; -alkynlene-Y-cycloalkyl; -alkylene-Y-heterocyclyl; -alkenylene-Y-heterocyclyl; -alkynlene-Y-heterocyclyl; —Y-alkyl; —Y-aryl; —Y-alkylene-aryl; —Y-alkylene-$NR_{11}R_{12}$; —Y—O—Si-(alkyl)$_3$; and —Y—O—Si-(alkylene-aryl)$_3$;

wherein

Y is —$CH_2$—, —C(O)—, —O—, —N(H)—, —S—, —S(O)—, —S($O_2$)—, —CON(H)—, —NHC(O)—, —NHCON(H)—, —NHS($O_2$)—, —S($O_2$)N(H)—, —C(O)—O—, —NHS($O_2$)NH—, or —O—CO—; and $R_{11}$ and $R_{12}$ are independently selected from the group consisting of: hydrogen, aryl, alkyl, and alkylene-aryl; or $R_{11}$ and $R_{12}$ are taken together to form a ring having the formula —$(CH_2)_q$-Q-$(CH_2)_r$— bonded to the nitrogen atom to which $R_{11}$ and $R_{12}$ are attached, wherein q and r are, independently, 1, 2, 3, or 4; Q is —$CH_2$—, —C(O)—, —O—, —N(H)—, —S—, —S(O)—, —$SO_2$—, —CON(H)—, —NHC(O)—, —NH-CON(H)—, —$NHSO_2$—, —$SO_2$N(H)—, —(O)CO—, —$NHSO_2$NH—, —OC(O)—, —N($R_{13}$)—, —N(C(O)$R_{13}$)—, —N(C(O)NH$R_{13}$)—, —N($SO_2$NH$R_{13}$)—, —N($SO_2R_{13}$)—, or —N(C(O)O$R_{13}$)—; or $R_{11}$ and $R_{12}$ are taken together, with the nitrogen atom to which they are attached, to form a heterocyclyl or heteroaryl ring;

$R_9$, $R_{10}$, and $R_{13}$ are independently selected from the group consisting of hydrogen, aryl, alkyl, and alkylene-aryl;

$A_1$ and $A_2$ are N—$R_{14}$, where $R_{14}$ is
(a) alkyl; or
(b) -alkylene-aryl $R_{17}$ and $R_{18}$ are independently selected from the group consisting of hydrogen, alkyl, and halogen;

$Ar_1$ and $Ar_2$ are phenyl;

or a pharmaceutically acceptable salt, solvate or prodrug thereof.

2. The compound of Formula (I) of claim 1, wherein $R_1$ and $R_2$ are independently selected from the group consisting of: 1-methylindol-3-yl; 4-chloro-1-methylindol-3-yl; 4-chloro-1-ethylindol-3-yl; 4-chloro-1-butylindol-3-yl; 4-chloro-1-benzylindol-3-yl; and 4-chloro-1-benzylindol-3-yl.

3. The compound of Formula (I) of claim 1, wherein at least one of $R_6$, $R_6'$, $R_7$, $R_7'$, $R_8$, and $R_8'$ is halogen.

4. The compound of Formula (I) of claim 1, wherein $R_6$, $R_6'$, $R_7$, $R_7'$, $R_8$, and $R_8'$ are independently selected from the group consisting of hydrogen, halogen, alkyl, and —O-alkylene-phenyl group.

5. A compound selected from the group consisting of: Bis(1-methylindol-3-yl)-(5-hydroxymethyl-2-furyl)methane, Bis(4-chloro-1-methylindol-3-yl)-(5-hydroxymethyl-2-furyl)methane, Bis(1-methylindol-3-yl)-(5-methoxycarbonylmethoxymethyl-2-furyl)methane, Bis(1-methylindol-3-yl)-(5-carboxymethoxymethyl-2-furyl)methane, and Bis(4-chloro-1-benzylindol-3-yl)-(5-hydroxymethyl-2-furyl)methane.

6. A pharmaceutical composition comprising a pharmaceutically acceptable carrier and a pharmacologically effective amount of a compound of the Formula:

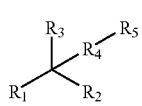
(I)

wherein

R₁ and R₂ are independently selected from the group consisting of

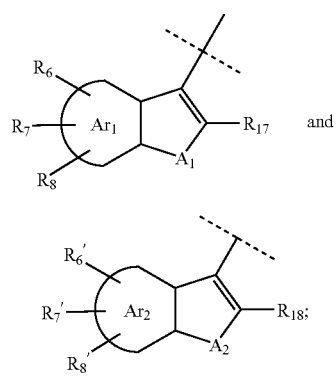

R₃ is
(a) hydrogen;
(b) alkyl;
(c) alkenyl; or
(d) alkynyl;
R₄ is heteroarylene;
wherein
R₄ is optionally substituted with a substituent of the formula

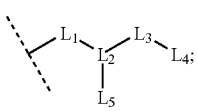

wherein
L₁ is a direct bond, alkylene, —O-alkylene-, alkylene-O—, —NH—C(O)—, —C(O)—NH— or —NH—CO—NH—;
L₂ is alkyline, alkenyline, heteroaryline, aryline, or heterocyclyline;
L₃ is —O—, —C(O)—N(R₁₉)—, —C(O)—O—, —C(O)—, or —N(R₁₉)—CO—N(R₂₀)—;
L₄ is H, alkyl, alkenyl, alkynyl, heterocyclyl, heteroaryl, alkylene-aryl;

L₅ is hydrogen, alkyl, alkenyl, alkynyl, -alkylene-aryl, -alkylene-heteroaryl, alkylene-O-alkylene-aryl, -alkylene-S-alkylene-aryl, -alkylene-O-alkyl, -alkylene-S-alkyl, -alkylene-NH₂, -alkylene-OH, -alkylene-SH, -alkylene-C(O)—OR₉, -alkylene-C(O)—NR₉R₁₀, -alkylene-NR₉R₁₀, -alkylene-N(R₉)—C(O)—R₁₀, -alkylene-N(R₉)—S(O₂)—R₁₀; or

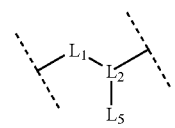

may be taken together to constitute a direct bond;
R₅ is
(a) hydrogen;
(b) alkyl;
(c) alkenyl;
(d) alkynyl;
(e) aryl;
(f) heteroaryl;
(g) cycloalkyl;
(h) heterocyclyl;
(i) alkylene-OH;
(j) alkylene-COOH;
(k) alkylene-NH₂;
(l) COOH;
(m) CONH₂; or
(n) NH₂;
R₆, R₆', R₇, R₇', R₈, and R₈' are independently selected from the group consisting of
(a) hydrogen;
(b) aryl;
(c) heteroaryl;
(d) heterocyclyl;
(e) cycloalkyl;
(f) halogen; and
(g) -alkylene-Y-aryl; -alkenylene-Y-aryl; -alkynylene-Y-aryl; -alkylene-Y-heteroaryl; -alkenylene-Y-heteroaryl; -alkynlene-Y-heteroaryl; -alkylene-Y-cycloalkyl-alkenylene-Y-cycloalkyl; -alkynlene-Y-cycloalkyl; -alkylene-Y-heterocyclyl; -alkenylene-Y-heterocyclyl; -alkynlene-Y-heterocyclyl; —Y-alkyl; —Y-aryl; —Y-alkylene-aryl; —Y-alkylene-NR₁₁R₁₂; —Y—O—Si-(alkyl)₃; and —Y—O—Si-(alkylene-aryl)₃;
wherein
Y is —CH₂—, —C(O)—, —O—, —N(H)—, —S—, —S(O)—, —S(O₂)—, —CON(H)—, —NHC(O)—, —NHCON(H)—, —NHS(O₂)—, —S(O₂)N(H)—, —C(O)—O—, —NHS(O₂)NH—, or —O—CO—; and
R₁ and R₁₂ are independently selected from the group consisting of: hydrogen, aryl, alkyl, and alkylene-aryl; or
R₁₁ and R₁₂ are taken together to form a ring having the formula —(OH₂)_q-Q-(CH₂)_r— bonded to the nitrogen atom to which R₁₁ and R₁₂ are attached, wherein q and r are, independently, 1, 2, 3, or 4; Q is —CH₂—, —C(O)—, —O—, —N(H)—, —S—, —S(O)—, —SO₂—, —CON(H)—, —NHC(O)—, —NH- —CON(H)—, —NHSO$_2$—, —SO$_2$N(H)—, —(O)CO—, —NHSO$_2$NH—, —OC(O)—, —N(R$_{13}$)—, —N(C(O)R$_{13}$)—, —N(C(O)NHR$_{13}$)—, —N(SO$_2$NHR$_{13}$)—, —N(SO$_2$R$_{13}$)—, or —N(C(O)OR$_{13}$)—; or R$_{11}$ and R$_{12}$ are taken together, with the nitrogen atom to which they are attached, to form a heterocyclyl or heteroaryl ring;

R$_9$, R$_{10}$, R$_{13}$, R$_{19}$, and R$_{20}$ are independently selected from the group consisting of hydrogen, aryl, alkyl, and alkylene-aryl;

A$_1$ and A$_2$ are N—R$_{14}$, where R$_{14}$ is
(a) alkyl; or
(b) -alkylene-aryl;

R$_{17}$ and R$_{18}$ are independently selected from the group consisting of hydrogen, alkyl, and halogen;

Ar$_1$ and Ar$_2$ are phenyl;

or a pharmaceutically acceptable salt, solvate or prodrug thereof.

7. The pharmaceutical composition of claim 6, in the form of an oral dosage or parenteral dosage unit.

8. The pharmaceutical composition of claim 6, wherein said compound is administered as a dose in a range from about 0.01 to 500 mg/kg of body weight per day.

9. The pharmaceutical composition of claim 6, wherein said compound is administered as a dose in a range from about 0.1 to 200 mg/kg of body weight per day.

10. The pharmaceutical composition of claim 6, wherein said compound is administered as a dose in a range from about 0.1 to 100 mg/kg of body weight per day.

11. The pharmaceutical composition of claim 6, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

12. The pharmaceutical composition of claim 6, wherein R$_1$ and R$_2$ of the compound of Formula (I) are independently selected from the group consisting of: 1-methylindol-3-yl; 4-chloro-1-methylindol-3-yl; 4-chloro-1-ethylindol-3-yl; 4-chloro-1-butylindol-3-yl; 4-chloro-1-benzylindol-3-yl; and 4-chloro-1-benzylindol-3-yl.

13. The pharmaceutical composition of claim 6, wherein R$_4$ in combination with R$_5$ is 5-carboxy-2-furyl; 5-hydroxymethylfuran-2-yl; or 5-methoxycarbonylmethoxymethyl-2-furyl.

14. The pharmaceutical composition of claim 6, wherein R$_6$, R$_6$', R$_7$, R$_7$', R$_8$, and R$_8$' of the compound of Formula (I) are independently selected from the group consisting of: hydrogen, halogen, alkyl, and —O-alkylene-phenyl.

15. The pharmaceutical composition of claim 6, wherein R$_1$ and R$_2$ are independently selected from the group consisting of: 1-methylindol-3-yl; 4-chloro-1-methylindol-3-yl; 4-chloro-1-ethylindol-3-yl; 4-chloro-1-butylindol-3-yl; 4-chloro-1-benzylindol-3-yl; and 4-chloro-1-benzylindol-3-yl; and R$_4$ in combination with R$_5$ is 5-carboxy-2-furyl; 5-hydroxymethylfuran-2-yl; or 5-methoxycarbonylmethoxymethyl-2-furyl.

16. The pharmaceutical composition of claim 6, wherein the compound of Formula (I) is selected from the group consisting of: Bis(1-methylindol-3-yl)-(5-hydroxymethyl-2-furyl)methane, Bis(4-chloro-1-methylindol-3-yl)-(5-hydroxymethyl-2-furyl)methane, Bis(1-methylindol-3-yl)-(5-methoxycarbonylmethoxymethyl-2-furyl)methane, Bis(1-methylindol-3-yl)-(5-carboxymethoxymethyl-2-furyl)methane, and Bis(4-chloro-1-benzylindol-3-yl)-(5hydroxymethyl-2furyl)methane.

* * * * *